United States Patent [19]
Christensen et al.

[11] 4,206,219
[45] Jun. 3, 1980

[54] 6- AND 1-SUBSTITUTED-1-CARBADETHIAPEN-2-EM-3-CARBOXYLIC ACID

[75] Inventors: Burton G. Christensen, Metuchen; David H. Shih, Edison, both of N.J.

[73] Assignee: Merck & Co., Inc., Rahway, N.J.

[21] Appl. No.: 954,274

[22] Filed: Oct. 24, 1978

[51] Int. Cl.² .................................. 544 92; 546 272; C07D 487/04; A61K 31/40
[52] U.S. Cl. .............................. 424/274; 260/239 A; 260/326.31; 260/345.7 R
[58] Field of Search .................... 260/376.31; 424/274

[56] References Cited
U.S. PATENT DOCUMENTS 3,950,357  4/1976  Kahan et al. ..................... 260/326.31
4,153,714  5/1979  Ponsford ......................... 260/326.31

Primary Examiner—Mary C. Lee
Attorney, Agent, or Firm—James A. Arno; Julian S. Levitt

[57] ABSTRACT

Disclosed are 6- and 1-substituted-1-carbadethiapen-2-em-3-carboxylic acids of the following structure:

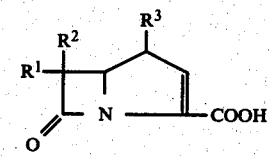

wherein $R^1$, $R^2$ and $R^3$ are, inter alia, independently selected from the group consisting of hydrogen, alkyl, aryl, and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotics effect is indicated.

4 Claims, No Drawings

6- AND 1-SUBSTITUTED-1-CARBADETHIAPEN-2-EM-3-CARBOXYLIC ACID

BACKGROUND OF THE INVENTION

This invention relates to 6- and 1-substituted-1-carbadethipen-2-em-3-carboxylic acids and the pharmaceutically acceptable salt, ester and amide derivatives thereof, which compounds are useful as antibiotics and which may be represented by the following generic structural formula (I):

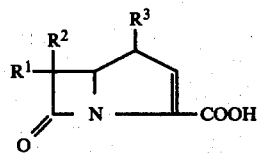

wherein $R^1$, $R^2$ and $R^3$ are independently selected from the group consisting of hydrogen, substituted and unsubstituted: alkyl, cycloalkyl, cycloalkylalkyl, alkylcycloalkyl, aryl, aralkyl, heteroaryl, heteraralkyl, heterocyclyl and heterocyclylalkyl wherein the substituent or substituents relative to the above named radicals are selected from the group consisting of amino, hydroxy, alkoxyl, mercapto, alkylthio, arylthio, sulfamoyl, amidino, guanidino, nitro, chloro, bromo, fluoro, cyano and carboxyl; and wherein the hetero atom in the above-named heterocyclic moiety is selected from the group consisting of oxygen, nitrogen and sulphur.

This invention also relates to the pharmaceutically acceptable salt, ester and amide derivatives of the compounds of the present invention identified by structure I, above.

This invention also relates to processes for the preparation of such compounds (I); pharmaceutical compositions comprising such compounds, and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyrogenes,* and *B. subtilis,* and gram negative bacteria such as *E. coli,* Pseudomonas, *Proteus morganii,* Serratia and Klebsiella. Further objects of this invention are to provide chemical processes for the preparation of such antibiotics and the non-toxic pharmaceutically acceptable salt, ester and amide derivatives thereof; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

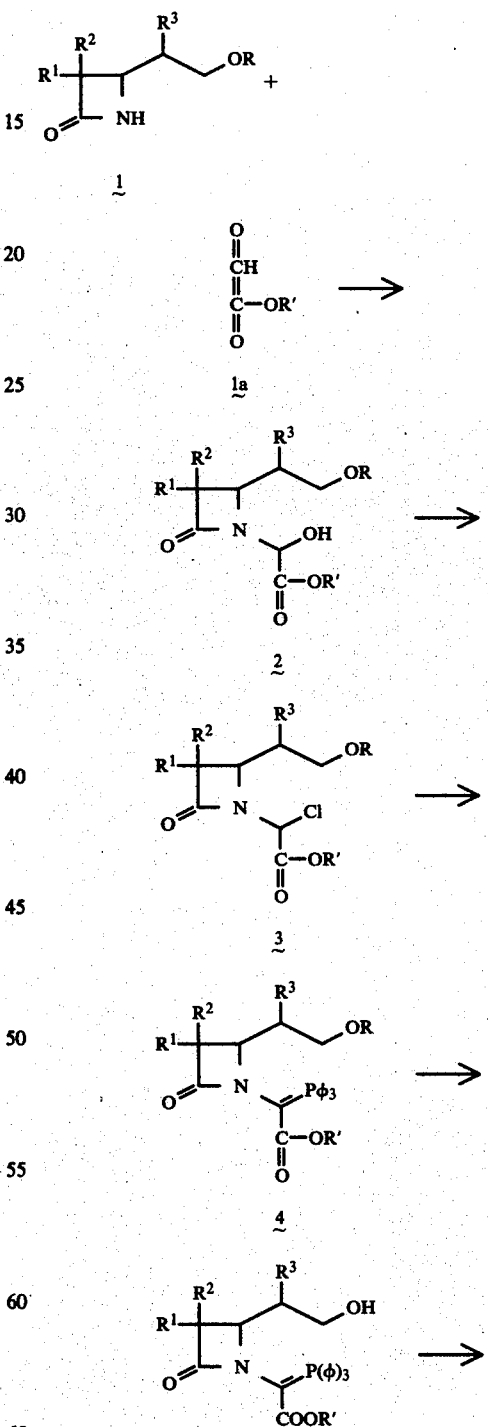

-continued

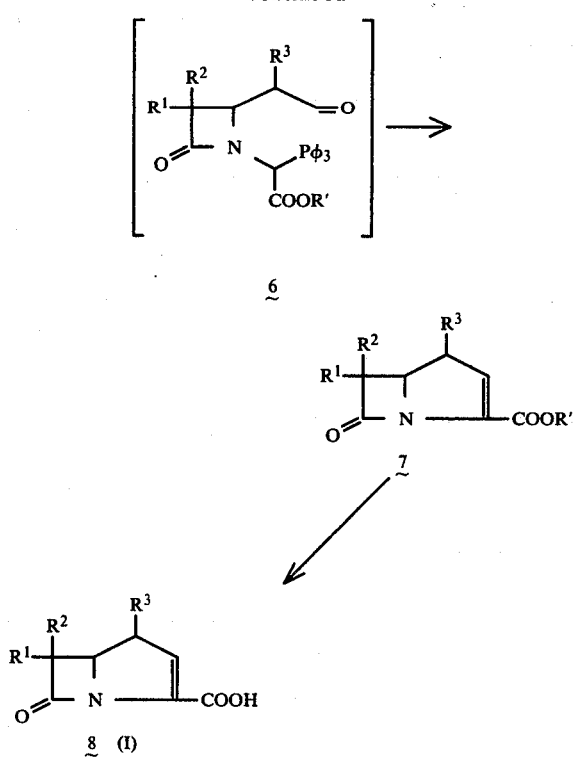

wherein R¹, R² and R³ are as defined; R and R' are readily removable blocking groups; R' may also be a pharmaceutically acceptable ester moiety. Typically, the blocking group R is an acyl such as a lower alkanoyl, aralkylcarbonyl or the like such as acetyl, bromo-t-butoxycarbonyl, benzyloxycarbonyl, formyl, trifluoroacetyl and the like or a trialkylsilyl such as a trimethylsilyl or t-butyl dimethylsilyl group; and typically the blocking group R' is substituted or unsubstituted alkyl, aralkyl, alkenyl, or the like such as benzyl, p-nitrobenzyl, o-nitrobenzyl, pivaloyloxymethyl, bromo-t-butyl and the like.

In words relative to the above reaction diagram, a suitably substituted azetidinone (1) is reacted with a glyoxalate ester such as benzyl glyoxalate to form the corresponding 1-(benzyloxycarbonylhydroxymethyl-)azetidinone (2). The reaction 1→2 is conveniently carried out in a solvent such as benzene, toluene, xylene and the like at a temperature of from about 25° C. to reflux for from 2 to 10 hours. There is no criticality as to the precise identity of the solvent, provided only that it adequately solubilizes the reactants and be inert or substantially inert to the desired course of reaction. The halogenation reaction 2→3 may be conducted by any of a variety of well-known halogenation means. Suitable reagents include: SOCl₂, POCl₃, oxalyl chloride and the like. A preferred means of chlorination involves treating 2 in a solvent such as tetrahydrofuran (THF), ether, CH₂Cl₂ and the like with thionylchloride in the presence of 1 to 2 equivalents (relative to the thionylchloride) of a base such as pyridine, triethylamine, guinoline and the like. Typically, the reaction is conducted at a temperature of from −30° to 25° C. for from 0.5 to 1 hour. The resulting 1-(benzyloxycarbonylchloromethyl)-azetidinone species, 3, is isolated, if desired, by conventional procedures for later reaction 3→4. The intermediate 4 is prepared from 3 by treating 3 in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl)phosphine or the like. Typically the reaction is conducted under a nitrogen atmosphere at a temperature of from −20° to 25° C., for for from 0.5 to 2 hours. The reaction 4→5 may be achieved by any of a variety of well-known deblocking procedures such as hydrolysis or hydrogenolysis. A particularly convenient means for the deblocking 4→5, when R=acyl, is by an alcoholysis procedure comprising treating 4 in a lower alkanol such as methanol, ethanol, or the like in the presence of 0.1 to 1.4 equivalents of the corresponding alkali metal alkoxide such as sodium methoxide or the like; typically the reaction is conducted at a temperature of from 0° to 25° C., for from 0.5 to 2 hours or is by an acid hydrolysis by treating 4 (R=triorganosilyl) with HCl in THF, DMF, or the like at 25° C. for 1 to 15 minutes. The ring closure reaction 5→7 proceeds via the oxo intermediate 6 and is achieved by treating 5 with an equivalent of an oxidizing system such as 1:1 mixture of dimethylsulfoxide (DMSO) and acetic anhydride (Ac₂O); other oxidizing systems include cyclohexylcarbodiimide in DMSO, CrO₃.2(pyridine) in CH₂Cl₂, and pyridinum chlorochromate in CH₂Cl₂ for example. Typically, the closure step 5→7 is conducted at a temperature of from about 0° to 100° C. for from 0.25 to 24 hours in the oxidative system (DMSO/Ac₂O) described above or by heating from 100°-160° C. (after isolation of the oxo compound 6) in a solvent such as benzene, toluene, dioxane, xylene, or DMF. The carboxyl deblocking step 7→8 may be achieved by a number of well-known procedures such as hydrolysis, hydrogenation, or photolysis of a suitable R' group. Suitable hydrogenation catalysts for deblocking include the platinum metals and their oxides such as palladium on carbon and the like; suitable solvents for the hydrogenation include methanol, dioxane/H₂O, ethanol/H₂O and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like. The carboxyl deblocking can also be achieved by photolysis of 7 in dioxane/H₂O, methanol/H₂O or ethanol/H₂O under u.v. radiation (λ=350 nm) for 1 to 4 hr. at 25° C.

The glyoxalate esters 1a used to react with 1 can be prepared by oxidation of the corresponding tartaric acid diesters with oxidants such as periodic acid or lead tetracetate in a solvent such as THF, benzene, or methylene chloride at −20° to 25° for ½ to 4 hours. The tartarate esters are prepared from dilithio tartarate or disodio tartarate by reaction with R'X wherein X is chloro, bromo or iodo and R' is as defined above in a solvent such as DMF or DMSO at 25° to 70° C. for from 4 to 48 hrs. As noted above, R' may be pharmaceutically acceptable ester moiety. Such pharmaceutically acceptable esters and amides, however, may also be prepared from the free acid of I according to the procedure of co-pending U.S. Patent Application Ser. No. 861,314 filed Dec. 16, 1977, which is directed to the pharmaceutically acceptable ester and amides of thienamycin and their preparation. Accordingly, for its disclosure relative to such pharmaceutically acceptable forms and their means of preparation, the above-cited application is incorporated herein by reference.

The following diagram summarizes the synthesis of substituted azetidinone material, 1.

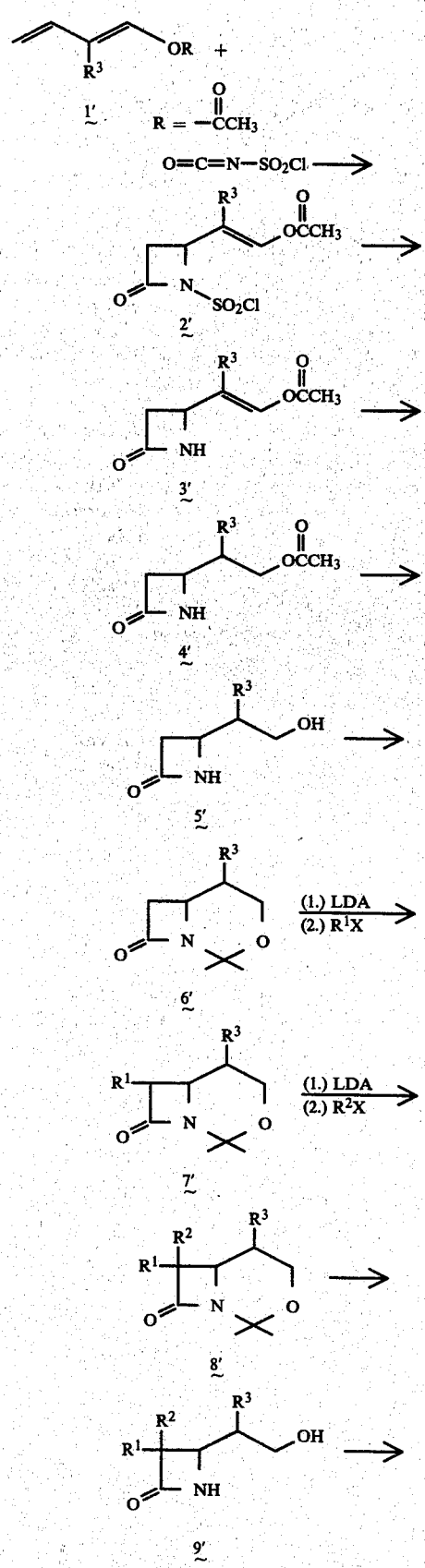

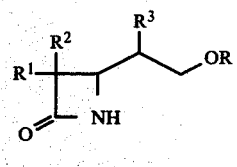

In words relative to the above diagram for the preparation of 1, the 4-(1-methyl-2-acetoxyvinyl)acetidinone-2-one (3') is prepared by reacting chlorosulphonyl isocyanate and an acyloxybutadiene (1') such as 1-acetoxy-2-methylbutadiene in a solvent such as anhydrous diethyl ether at a temperature of from about −30° C. to 0° C. under a nitrogen atmosphere. The reaction intermediate 2' is converted to 3' by hydrolysis. The reduction of 3' to provide the 4-(1-methyl-2-acetoxyethyl)-2-azetidinone (4') is conducted by any convenient means such as hydrogenation in the presence of a catalyst such as platinum, palladium or oxides thereof under a hydrogen pressure of from 1 to 20 atmospheres in a solvent such as ethanol, ethylacetate, or the like, at a temperature of from 0° to 25° C. for from 5 minutes to 1 hour. The 4-(2-hydroxy-1-methyl-ethyl)-2-azetidinone species 5' is obtained from 4' by hydrolysis. The 8-oxo-2,2-dimethyl-5-methyl-3-oxa-1-azabicyclo[4.2.0]octane species 6' is obtained on treatment of 5' with 2,2-dimethoxypropane in the presence of a catalyst such as boron trifluoride etherate in a solvent such as methylene chloride at a temperature of from 0° to 40° C. for from 1 to 40 minutes. Alternatively, 5' can be treated with boron trifluoride etherate and trimethylorthoformate to give 8-oxo-2-methoxy-5-methyl-3-oxa-1-azabicyclo[4.2.0]octane which can be mono- or dialkylated following the procedures for 6'→7' or 8'. Alkylation of 6' provides 7'. Typically, 6' is treated with a strong base such as lithium diisopropylamide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, $R^1X$ is added ($R^1$ is as described above and X is chloro or bromo; alternatively the alkylating agent may be $R^1$-tosylate, $R^1$-mesylate or an aldehyde or ketone such as acetaldehyde and the like) to provide mono- alkylated species 7'. When desired dialkylated species 8' may be obtained from 7' by repeating the alkylating procedure, 6'→7'. Species 9' is obtained from 7' or 8' by acid hydrolysis.

The desired blocked-species 1 is obtained by treating 9 with an silylating agent such as t-butyldimethylchlorosilane, trimethylchlorosilane and the like in a solvent such as DMF, $CH_2Cl_2$, THF or the like in the presence of a base such as imidazole or the like at 0° C. to 25° C. for from 0.5 hr to 6 hr or with an acylating agent such as acetyl chloride, formic acetic anhydride, trifluoroacetic anhydride and the like in a solvent such as $CH_2Cl_2$, $CHCl_3$, THF and the like at a temperature of from −20° to about 25° C. for from 0.5 to about 4 hours. The starting material 1 may be isolated for later reaction in accordance with the procedures of the present invention for the preparation of the compounds of the present invention.

It should be noted that in the establishment of R (9'→1), the ring nitrogen may be protected by an easily removable blocking group R":

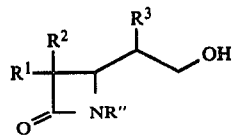

wherein R" is acyl or triorganosilyl such as trimethylsilyl, t-butyldimethylsilyl, trifluoroacetyl, formyl, or the like. Removal of R" is accomplished by hydrolysis to provide 1 according to well-known procedures.

Starting material 1 may alternatively be prepared by the following scheme:

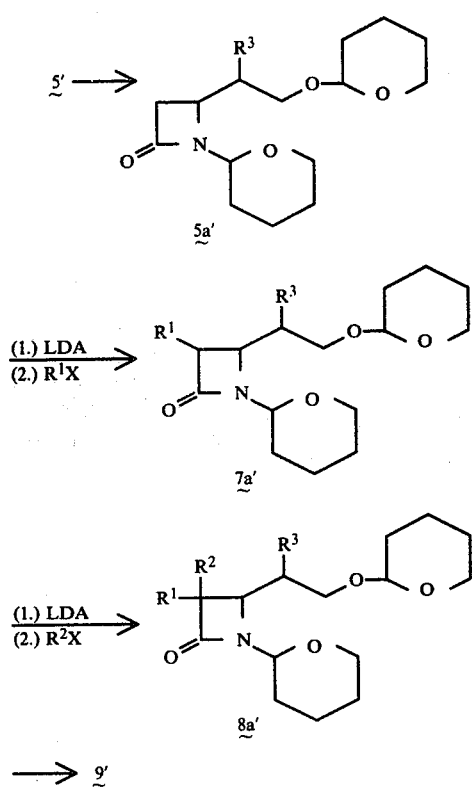

wherein all symbolism is as previously defined.

Reaction 5′→5a′ is accomplished by treating 5′ with 2,3-dihydropyran in a solvent such as p-dioxane benzene, and the like in the presence of p-toluenesulfonic acid, perchloric acid, or the like at a temperature of from 0° to about 30° C. The intermediate 5a′ may be isolated for later alkylation to obtain 7a′ and 8a′ by procedures analogous to previously described reactions 6′→7′→8′. Intermediate species 9′ is obtrained from 7a′ or 8a′ by mild acid hydrolysis.

Finally, it should be noted that intermediate species 9a′ may conveniently be prepared for later reaction in the above scheme by internal acylation according to the following reaction:

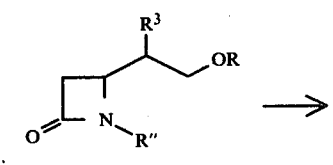

-continued

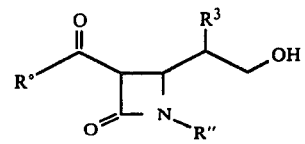

wherein R is acyl,

is $R^1$ and $R°$ is for example, lower alkyl, acyl, or the like. Typically, the above reaction is conducted in a solvent such as tetrahydrofuran, ether, dimethoxyethane, or the like in the presence of 1 to 2 equivalents of a strong base such as lithium diisopropylamine, sodium hydride, potassium hydride or the like at a temperature of from −78° to 25° C., for from 0.5 to 24 hours.

It will be recognized that the compounds of the present invention, structure I, above, exhibit stereoisomerism. The nature of which depends upon the identity of ring substituents $R^1$, $R^2$ and $R^3$. The total synthesis of I is capable of stereo-selectivity. Preferably the paths leading the ultimate diastereomers of I diverge at intermediate level 6′, 7′ or 8′ (see above reaction diagram). Fractional crystallization or practically any chromatographic technique is suitable for resolving the diastereoisomers at the preferred intermediate level. Completion of the synthesis after such resolution provides, if desired, the diastereoisomers of I in substantially pure form. A representative example of such resolution is presented below in the Examples section.

Preparation of the Substituted Acyloxy-butadiene, 1′

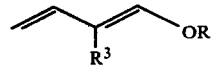

The substituted 1,3-butadiene reagent 1′ is prepared according to known procedures, which may be summarized:

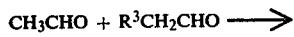

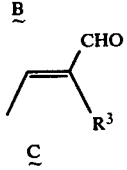

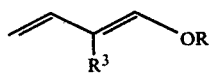

wherein $R^3$ and R are as defined above. The $\alpha,\beta$-unsaturated aldehyde intermediates C is prepared on condensation of A and B in the presence of a base such as NaOH, or the like at a temperature of from 0° to 100° C. for from 10 min. to 2 hours. Condensation of C with the isopropenyl ester D in the presence of cupric acetate (1 to 10 mole percent relative to C) and a strong acid such as p-toluene sulfonic acid, perchloric acid, sulfuric acid or the like (1 to 10 mole percent relative to C) provides 1'. Typically the reaction is conducted at 90° to 120° C. for from 1 to 8 hours. Representative examples illustrating this preparation of 1' are given below.

In the generic description of the present invention (I, above), the substituents $R^1$, $R^2$ and $R^3$ are preferably selected from the group consisting of hydrogen; substituted and unsubstituted: straight and branched loweralkyl having from 1 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent (or substituents) relative to the above-named radicals is selected from the group consisting of amino, hydroxyl, cyano, carboxyl, nitro, chloro, bromo, fluoro, lower alkoxy having from 1 to 6 carbon atoms, mercapto, perhaloloweralkyl such astrifluoromethyl, loweralkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

A particularly preferred class of compounds are those wherein $R^2$ is hydrogen, $R^3$ is selected from the group consisting of substituted and unsubstituted: loweralkyl having from 1 to 6 carbon atoms, cyclopropyl, benzyl and phenyl; and $R^1$ is an $\alpha$-substituted alkyl wherein the $\alpha$-substituent is hydroxyl, amino or mercapto and wherein the alkyl moiety is straight or branched and comprises 1 to 6 carbon atoms; the substituents relative to the above-named preferred radicals are selected from the group consisting of hydroxyl, bromo, fluoro, chloro, amino, amidino, guanidino, phenyl, mercapto, carboxyl, trifluoromethyl, loweralkylthio and loweralkoxyl wherein the alkyl moiety of the loweralkylthio and loweralkoxyl comprises 1 to 6 carbon atoms.

The preferred esters used as protecting groups are those where R' is benzyl, p-nitrobenzyl, o-nitrobenzyl, t-butyl, bromo-t-butyl, t-butyl-dimethylsilyl, trimethylsilyl, trichloroethyl; or R' represents pharmaceutically acceptable ester moieties such as pivaloyloxymethyl, allyl, methallyl, (2-methylthio)-ethyl, 3-methyl-2-butenyl, p-t-butylbenzyl, 5-indanyl, 3-phthalidyl.

The compounds made available by the present invention are valuable antibiotics active against various gram-positive and gram-negative bacteria and, accordingly, find utility in human and veterinary medicine. Such sensitive bacteria representatively include: *Staphylococcus aureus*, *Escherichia coli*, *Klebsiella pneumoniae*, *Serratia*, *Salmonella typhosa*, Pseudomonas and *Bacterium proteus*. The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing an/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder, liquid sprays, inhalants, lozenges, or throat paints. For medication of the eyes or ears, the preparations may be presented as individual capsules, in liquid or semi-solid form, or may be used as drops. Topical applications may be formulated in hydrophobic or hydrophilic bases as ointments, creams, or loations.

Also, in addition to a carrier, the instant compositions may include other ingredients such as stabilizers, binders antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in U.S. patent application Ser. No. 861,314 (filed 12-16-77), which application is directed, inter alia, to pharmaceutically acceptable salts and esters of the carboxyl group of thienamycin. It is precisely these salts and esters which are preferred in the present invention and they are prepared in a manner analogous to that disclosed in U.S. patent application Ser. No. 861,314, which is incorporated herein by reference. Thus, especially preferred salts include sodium, potassium, ammonium, and the like; and especially preferred esters include pivaloxymethyl p-t-butylbenzyl, 5-indanyl, 3-phthalidyl, 3-methyl-2-butenyl, and the like. One should note that when, in the total synthesis outlined above, R' is a pharmaceutically acceptable ester moiety, there is no need for the final deblocking step if it is desired to have the final product I in the form of a pharmaceutically acceptable ester.

The following Examples illustrate but do not limit the product, process, compositional or method of treatment aspects of the present invention. All reaction temperatures are in °C.

EXAMPLE 1a

Preparation of Di-o-nitrobenzyltartarate

Tartaric acid (15.0 g, 0.1 mole) is dissolved in 40 ml. water and treated with lithium hydroxide (8.4 g, 0.2 mole). The resulting solution is evaporated to a small volume under reduced pressure and the residue is treated with p-dioxane. The resulting precipitate is filtered and dried under vacuum to give the di-lithium tartarate (17.7 g).

Di-lithium tartarate (9.46 g, 0.0585 mole) is suspended in 200 ml. DMF and treated with o-nitrobenzyl chloride (20 g, 0.117 mole) and sodium iodide (17.5 g, 0.117 mole). The mixture is stirred under $N_2$ for 2½ days at 65° C.

The solvent is removed under vacuum and the resulting paste is treated with water and sodium thiosulfate (5 g). The resulting solid is filtered and dried to give di-o-nitrobenzyltartarate (17.0 g, 0.040 mole, 69%, m.p. 128° C.).

n.m.r. (DMSO): 4.8 d(j=7, H-C-OH), 5.23 d(j=7, H-C-OH), 5.7 S((O-CH$_2$-C$_6$H$_4$-NO$_2$); 7.73 & 8.2 m (aromatic H).

Similar treatment of the di-lithium salt with R'X (where X=Cl, Br or I) such as p-nitrobenzylbromide, benzylbromide, pivalyoxymethyl chloride gives the corresponding di-ester of tartaric acid such as di-p-nitrobenzyl tartarate, di-benzyl tartarate, dipivaloyloxymethyl tartarate. These can be used as equivalent alternates to di-o-nitrobenzyl tartarate in Example 2, below.

EXAMPLE 1

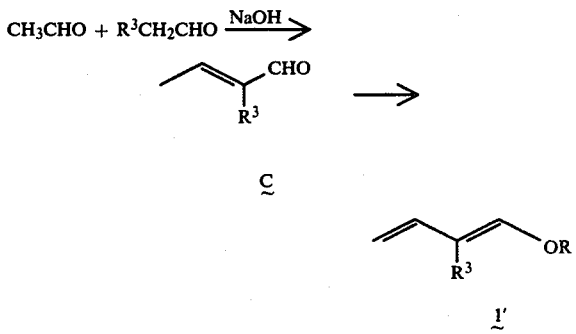

The α,β-unsaturated aldehydes (C) are prepared by modified procedures reported by M. B. Green and W. J. Hickinobottom in *J. Chem. Soc.* 3262 (1957); and W. J. Bailey and R. Barclay Jr., *Org. Chem.*, 21, 328 (1956).

Acetaldehyde (1 eq.) and propionaldehyde ($R^3$=CH$_3$) (1 eq.) are placed in a three-necked round-bottom flask which is equipped with a mechanical stirrer, a dry-ice condenser, and a pressure equalized dropping-funnel. To the solution is added dropwise 1 eq. of 1 N NaOH through the dropping funnel with constant stirring. After completion of the mixing, the mixture is stirred for 10 min, then poured into a beaker containing crushed ice. Extraction of the mixture with ether gives the crude product. The desired product (C) is obtained by fractional distillation through a Widmer column.

Isopropenyl acetate (2 eq), cuprous acetate (0.002 eq) p-toluenesulfonic acid (0.008 eq.) and the α,β-unsaturated aldehyde C(1 eq.) are placed in a three-necked round-bottom flask equipped with a thermometer, a nitrogen inlet tube and a Widmer column which is attached with a distillation head. The mixture is heated at 93°–110° C. until quantitative acetate is collected. The mixture is then allowed to cool to r.t. and filtered from solids. The dark brown filtrate is mixed with triethanolamine in water at 0° C. The two layer mixture is distilled quickly under reduced pressure. The organic layer of the distillate is separated. The aqueous layer is extracted with 200 ml ether. The combined organic layer is washed with 10% K$_2$CO$_3$, dried over Na$_2$SO$_4$, and evaporated in vacuo. The residue so obtained is mixed with 2.0 g N-phenyl-β-naphthamine and distilled under reduced pressure to give the desired 2-substituted 1-acetoxy-1,3-butadiene (1').

Following the procedure of Example 1, the following $R^3$ substituted species are obtained. (Table I).

TABLE I

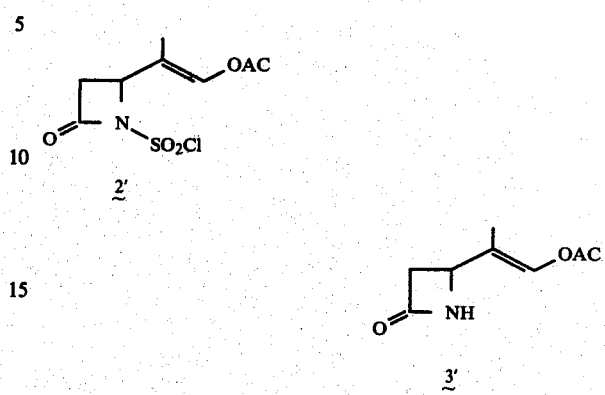

| | R³ | R |
|---|---|---|
| 1. | CH₃ | CH₃C(=O)— |
| 2. | CH₃CH₂ | CH₃C(=O)— |
| 3. | CH₃CH₂CH₂ | CH₃C(=O)— |
| 4. | (CH₃)₂CH | CH₃C(=O)— |
| 5. | cyclopropyl | CH₃C(=O)— |
| 6. | Ph (Ph = phenyl) | CH₃C(=O)— |
| 7. | PhCH₂ | CH₃C(=O)— |

EXAMPLE 2

Preparation of 6-(1-hydroxyethyl)-1-methyl-1-carbadethiapen-2-em-carboxylic acid

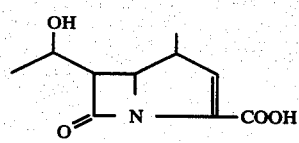

Step A

Preparation of 1'

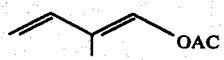

Isopropenyl acetate (182 g), cupric acetate (0.40 g), 2-methyl-2-butenal (84 g) and p-toluenesulfonic acid (1.52 g) are placed in a 1.0-1, three-necked flask eqiupped with a thermometer, a nitrogen inlet tube and a 10-in. Widmer column which is attacked with a distillation head. The mixture is heated at 93°–110° C. until 73 ml of acetone is collected. After cooling to r.t. (25° C.) the mixture is filtered from solids. The dark brown filtrate is cooled in an ice-bath and mixed with 3.4 g triethanolamine in 200 ml water. The two layer mixture is distilled quickly at 53 mm (b.p. 54° C.). The organic layer of the distillate is separated. The aqueous layer is extracted with 200 ml ether. The organic layers are combined and washed with 10% $K_2CO_3$, dried over $Na_2SO_4$, and evaporated in vacuo. The residue so obtained is mixed with 2.0 g N-phenyl-β-naphthamine and distilled under reduced pressure to give 1' (97 g), b.p. 81°–91° (66 mm).

Step B

Preparation of 2' and 3'

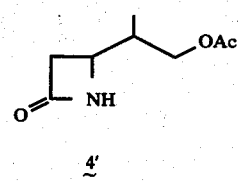

Chlorosulfonylisocyanate (CSI) (6.5 ml) is placed in a three-necked, 100-ml flask equipped with a thermometer, a magnetic stirring bar, a nitrogen inlet tube and a 25-ml pressure-equalized dropping funnel. The CSI is chilled to −50° C. and mixed with 12.5 ml ether through the dropping funnel. The etheral solution of CSI is allowed to warm up to −25° C.; to the solution is added dropwise 1-acetoxy-2-methyl-1,3-butadiene (1') (5.9 ml in 12.5 ml ether) in 30 min. The mixture is then stirred for 20 min at −20°±3° C. The white precipitate formed initially is redissolved at the end of the reaction.

In a 500-ml round flask, a solution of 10 g sodium sulfite and 25 g potassium hydrogen phosphate in 100 ml water is prepared and is cooled in an ice bath. Ether (100 ml) and crushed ice (100 g) are added and the mixture is vigorously stirred in an ice bath. At the end of 20 minutes reaction time, the reaction mixture which contains 2' is transferred into the dropping funnel and added dropwise to the hydrolysis mixture in 5 minutes. The hydrolysis is allowed to continue for an additional 30 minutes at 3° C. The organic layer is separated and the aqueous is extracted with 50 ml ether. The organic layers are combined, dried over $Na_2SO_4$ and evaporated to give crystalline product 3' (2.3 g), m.p. 77°–78,5°; m.s. 169(M+); IR 1760 cm⁻¹ (β-lactam); NMR (300 MHz, CDCl₃): 1.70 (d), 2.16(s), 2.84 (qq), 3.18 (qq), 4.20 (m), 5.82 (broad, and 6.26 (s) ppm.

Step C

Preparation of 4'

4-(1-methyl-2-acetoxyvinyl)azetidine-2-one (3') (6.5 g) is hydrogenated on a Parr shaker at r.t. under 40 psi hydrogen in the presence of 10% Pc/C (0.6 g) in 200 ml ethylacetate for 2 hr. The mixture is filtered from the catalyst and the filtrate is evaporated in vacuo to give the crude product. Purification of the crude product by high pressure liquid chromatograph (HPLC) (silical gel column, 30% ethylacetate/CH₂Cl₂ solvent system) affords a white crystalline product 4' (6.04 g) after evaporation of solvent. The product shows following physical characteristics: ms 171 (M+); IR(Neat) 1754 cm$^{-1}$; NMR (60 MHz, CDCl$_3$): 0.96 (d), 1.01 (d), 2.06 (d, OAc), 2.75–3.80 (m), 3.99 (d) and 6.80 (broad) ppm.

STEP D

Preparation of 5'

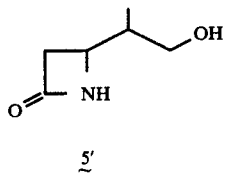

5'

Under N$_2$ at 0°, a solution of 4-(1-methyl-2-acetoxyethyl)-2-azetidinone 4' (1.2 g) in 10 ml methanol is treated with sodium methoxide (57 mg). After stirring for 1 hr, the solution is neutralized with glacial acetic acid (65 mg). Removal of methanol in vacuo gives crude 4-(1-methyl-2-hydroxyethyl)-2-azetidinone (5') as an oil. The product is purified by chromatography on silica gel eluting with ethyl acetate and gives 0.78 g of 5':

IR (neat): 1740 cm$^{-1}$; NMR (CDCl$_3$): 0.77 (d), 0.96 (d), 1.90 (m), 2.60–3.30 (m), 3.60 (m), 4.19 (s), and 7.23 (s). The product crystallizes as colorless solids in the refrigerator.

STEP E

Preparation of 6'

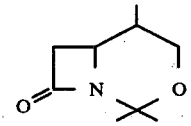

6'

A solution of 4-(1-methyl-2-hydroxyethyl)-2-azetidinone (0.5 g) and 2,2-dimethoxypropane (0.48 g) in 10 ml anhydrous methylene chloride is treated with boron trifluoride (55 mg) at room temperature for 90 min. The mixture is washed with 5 ml saturated NaHCO$_3$. The organic layer is separated, dried over Na$_2$SO$_4$ and allowed to evaporate in vacuo to give crude isomeric mixture of 6' (0.48 g) as an oil.

Separation of isomers 6'α and 6'β is accomplished by high pressure liquid chromatograph (HPLC) (silica gel) eluting with 40% ethylacetate/hexanes. After evaporation of the solvents affords 150 mg of 6'β as an oil and 200 mg of 6'α as a white solid.

NMR (300 MHz, CDCl$_3$) of 6'α: 0.81 (d), 1.31 (s), 1.68 (s), 1.62 (m), 2.52 (q), 3.05 (m), 3.42 (t), and 3.66 ppm (q), NMR (300 MHz, CDCl$_3$) of 6'β: 1.10(d), 1.38 (s), 1.67 (s), 1.90 (m), 2.80 (q), 2.86 (q), 3.62 (q), 3.78 (m) and 3.98 (q) ppm.

STEP Fa

Preparation of 7'α

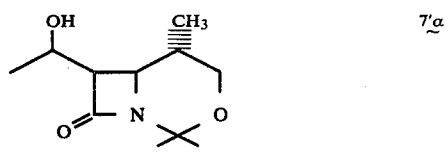

At −78° C., diisopropylamine (2.2 g) in 20 ml of anhydrous tetrahydrofuran is treated with n-butyllithium (1.6 M in n-hexane, 14 ml) for 5 min. To the solution is added 8-oxo-5α, 2,2-trimethyl-1-azabicyclo[4.2.0]octane (6'α) (3.4 g) and the mixture is stirred for 10 min. The resulting lithium enolate is treated with acetaldehyde (1.68 ml). The mixture is stirred for 1 min. then is quenched with 24 ml saturated ammonium chloride at −78° C., then allowed to warm to room temperature (25° C.). The mixture is extracted with ethylacetate (2×100 ml). The organic layer is separated, dried over Na$_2$SO$_4$ and allowed to evaporate in vacuo to give 4.5 g of the crude product 7'α.

The crude isomeric mixture of 7'α is purified and separated by HPLC (silica gel) eluting with 50% ethylacetate/methylene chloride to give 3.5 g of trans-7'α and 0.5 g of cis-7'α. Both isomers are crystalline solids.

STEP Fb

Preparation of 7'β

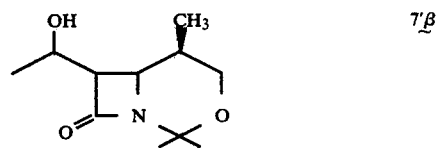

Following the procedure of Step Fa, except replacing the starting material 6'α with 6'β isomer, the products, trans-7'β (4.0 g) and cis-7'β (0.1 g), are obtained.

STEP Fc

Preparation of 7"β

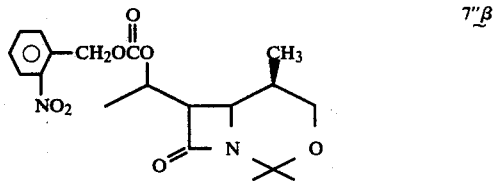

Under anhydrous conditions at 0° C. a solution of R enriched trans-7'β (2.90 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1 N HCl, water, brine and water. The organic layer is separated, dried over Na$_2$SO$_4$ and allowed to evaporate in vacuo to give crude products. The crude products dissolved in 20 ml ether and chilled at −5° C. give the o-nitrobenzyl alcohol (0.5 g) which is separated by filtration. The isomeric mixture trans-7"β is purified and separated by HPLC (silica gel) eluting with 40% ethylacetate/cyclohexane to give 1.2 g of S-trans-7″β and 1.0 g of R-trans-7″β.
The spectra data of R-trans-7″β: NMR (300 MHz, CDCl₃): 1.12 (d), 1.40 (s), 1.46 (d), 1.73 (s), 1.95 (m), 3.20 (q), 3.60 (q), 3.74 (q), 3.95 (q), 5.07 (m), 5.58 (q), 7.56 (t), 7.70 (m) and 8.19 (d)ppm.
The spectra data of S-trans-7″β: NMR (300 MHZ, CDCl₃): 1.10 (d), 1.40 (s), 1.43 (d), 1.72 (s), 1.94 (m), 3.34 (q), 3.61 (q), 3.67 (q), 3.96 (q), 5.13 (m), 5.64 (d), 7.53 (m), 7.68 (m), and 8.17 (d)ppm.
STEP Fd
Preparation of 7″α
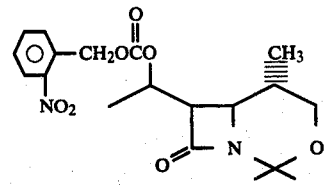
Following the procedure of Step Fc; except replacing the starting material trans-7′β with trans-7′α isomer, the products R-trans-7″α and S-trans-7″α are obtained.

TABLE II
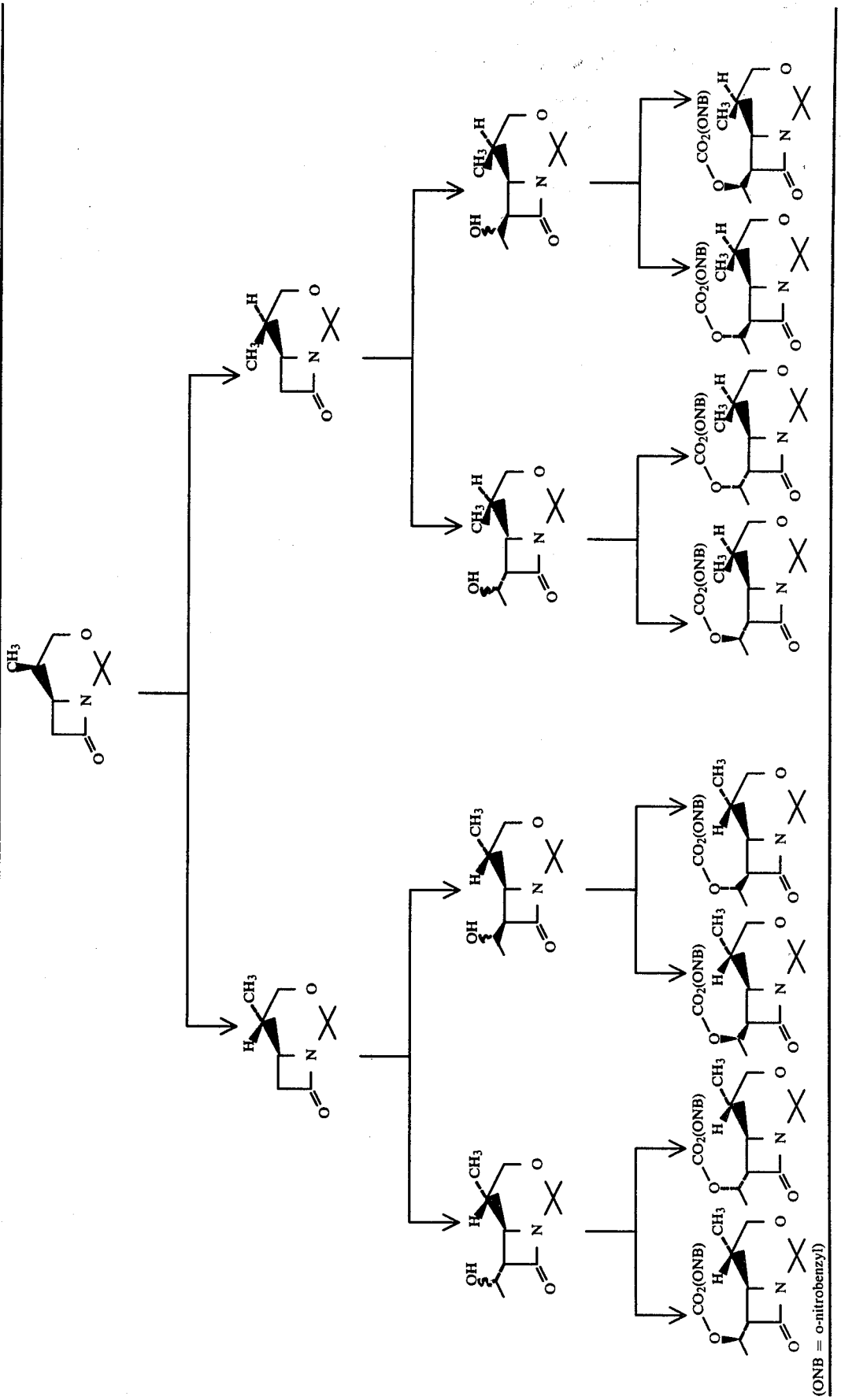
(ONB = o-nitrobenzyl)

STEP Ga

Preparation of R-trans-9'β

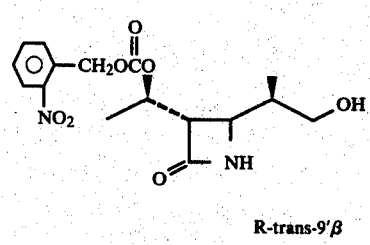

R-trans-9'β

8Oxo-3-oxa-5β-2,2-trimethyl-7α-(1R-o-nitrobenzyl-carbonyldioxyethyl)-1-azabicyclo[4.2.0]octane (R-trans-7"β) (2.1 g) is dissolved in 4 ml trifluoroacetic acid and 4 ml water at room temperature and the mixture is stirred for 10 minutes. The resulting homogeneous solution is slowly poured into a vigorously stirred saturated solution of potassium bicarbonate (30 ml) in a 200-ml beaker. The mixture is extracted with methylene chloride (200 ml). The organic layer is separated, dried over $Na_2SO_4$ and allowed to evaporate in vacuo to give crude product 9' which is purified by a silica gel column eluting with 40% ethylacetate/cyclohexane to afford product R-trans-9'β as an oil, NMR (300 MHz, $CDCl_3$): 0.98 (d), 1.28 (d), 2.85 (m), 3.20 (q), 3.62 (m), 5.12 (m), 5.57 (q), 6.40 (s), 7.53 (t), 7.66 (m) and 8.14 (d).

Step Gb

Following the procedure of Step Ga, except systematically replacing the starting material with the other isomers, the other isomeric products are obtained (Table III). (R is o-nitrobenzyloxycarbonyl.)

TABLE III

| Starting material | Product |
|---|---|
| S-trans-7"β | S-trans-9'β |
| R-trans-7"α | R-trans-9'α |
| S-trans-7"α | S-trans-9'α |
| R-cis-7"α | R-cis-9'α |
| S-cis-7"α | S-cis-9'α |
| R-cis-7"β | R-cis-9'β |
| S-cis-7"β | S-cis-9'β |

STEP Ha

Preparation of R-trans-1β

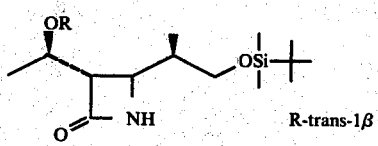

R-trans-1β

The starting material R-trans-9'β (1.58 g, 4.5 mmol) is treated with 5 equivalents of t-butyldimethylchlorosilane, 10 equivalents of imidazole in 5 ml anhydrous N,N-dimethylformamide (DMF) at room temperature for 3 hrs. The mixture is allowed to evaporate in vacuo to give crude product. Purification of the crude product by a silica gel eluting with 30% ethylacetate/cyclohexane gives 2.0 g of the product (R-trans-1β), NMR (300 MHz, $CDCl_3$): 0.04 (s), 0.88 (s), 0.98 (d), 1.26 (d), 1.82 (m), 3.20 (q), 3.60 (m), 5.15 (m), 5.59 (q), 5.94 (s), 7.54 (t), 7.68 (m) and 8.18 (d)ppm. (R is o-nitrobenzyloxycarbonyl.)

STEP Hb

Following the procedure of Step Ha except replacing the starting material, the other isomeric products are obtained (Table IV).

TABLE IV

| Starting Material | Product |
|---|---|
| S-trans-9'β | S-trans-1β |
| R-trans-9'α | R-trans-1α |
| S-trans-9'α | S-trans-1α |
| R-cis-9'α | R-cis-1α |

TABLE IV-continued

| Starting Material | Product |
|---|---|
| S-cis-9'α | S-cis-1α |
| R-cis-9'β | R-cis-1β |
| S-cis-9'β | S-cis-1β |

STEP I

Preparation of 2

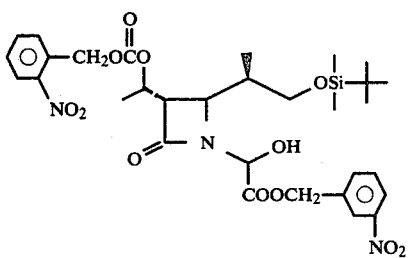

o-Nitrobenzyl-d-tartarate (1.8 g) is oxidized with periodic acid (0.97 g) in 18 ml of anhydrous tetrahydrofuran at 25° C. for 30 min. The mixture is filtered from solids and the filtrate is allowed to evaporate in vacuo to give o-nitrobenzylglyoxylate which is then taken up in 100 ml benzene and transferred into a 250-ml round bottom flask. To the solution is added trans-3-[1(R)-o-nitrobenzyloxycarbonyloxyethyl]-4-[1β-methyl-2-t-butyldimethylsilyoxy)ethyl]2-azetidinone (R-trans-1β) (2.0 g). The mixture is heated at reflux and water removed with a Dean-Stark trap packed with CaH₂ (1 g). for 6 hr. The mixture is cooled, filtered, evaporated and chromatographed on silica gel eluting with 30% ethylacetate/cyclohexane to give 2.

STEP J

Preparation of 3 and 4

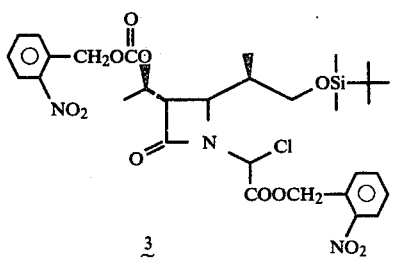

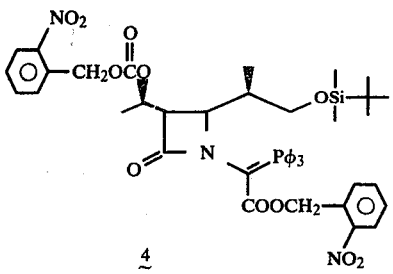

Trans-1-(o-nitrobenzyloxycarbonylhydroxymethyl)-3-[1(R)-o-nitrobenzyloxycarbonyloxyethyl]-4-[(1β-methyl-2-t-butyldimethylsilyloxy)ethyl]-2-azetidinone (2) (3.92 g) in 20 ml anhydrous tetrahydrofuran at −20° C. is treated with pyridine (0.42 ml) and thionyl chloride (0.37 ml). The mixture is allowed to warm to 25° C. with stirring, then filtered from solids. After removal of solvent in vacuo, product 3 is obtained. The chloride 3 is redissolved in 25 ml anhydrous DMF and treated with triphenylphosphine (1.1 g) with stirring at 25° C. for 1 hr. Solvent is removed in vacuo and the residue is dissolved in 100 ml methylene chloride and washed with 0.1 N pH 7.2 phosphate buffer 30 ml; chromatographic purification on silica gel, eluting with 40% ethylacetate/cyclohexane, gives product 4 (1.0 g), IR (CHCl₃): 1750 cm⁻¹ (β-lactam), 1620 cm⁻¹ (ylide ester).

STEP K

Preparation of 5

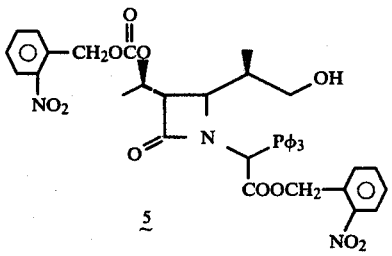

Trans-1-(o-nitrobenzyloxycarbonyltriphenylphosphoranylmethyl)-3-[1(R)-o-nitrobenzyloxycarbonyloxyethyl]-4-[1β-methyl-2-t-butyldimethylsilyloxy)ethyl]-2-azetidinone (4) (1.0 g) is dissolved in 10 ml tetrahydrofuran and is treated with conc. HCl (0.41 ml) at 25° C. for 10 min. The mixture is diluted with 200 ml methylene chloride then washed with 0.1 M Na₂HPO₄ (50 ml) The organic layer is separated, dried over Na₂SO₄ and evaporated in vacuo to give crude 5. Chromatographic pruification of the crude product eluting with 30% ethylacetate/cyclohexane gives 0.68 g of 5.

IR (CHCl₃): 1750 and 1610 cm⁻¹.

STEP L

Preparation of 7

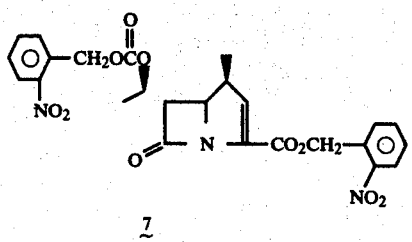

7

Trans-1-(o-nitrobenzyloxycarbonyltriphenylphos-phoranylmethyl)-3-[1(R)-o-nitrobenzyloxycarbonylox-yethyl]-4-[(1β-methyl-2-hydroxy)ethyl[-2-azetidinone(5) (70 mg) is treated with 1 ml DMSO and 1 ml acetic anhydride at r.t. overnight. After solvents evaporated in vacuo the residue is chromatographed on TLC plate (silica gel GF, 500μ) eluting with 50% ethylacetate/cyclohexane to give 12 mg of 7. IR (CHCl₃): 1770 cm⁻¹, and 1740 cm⁻¹; NMR (300 MHZ, CDCl₃): 1.15 (d); 2.80 (d), 3.30 (m), 3.53 (q), 4.35 (q), 5.21 (quintet), 4.55 (d), 4.82 (d), 4.55 (d), 4.62 (d), 6.51 (d) 7.49 (q), 7.65 (m), 7.83 (d) and 8.12 (m)ppm.

STEP Ma

Preparation of (I)

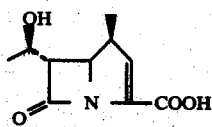

(I)

Trans-6-[1(R)-o-nitrobenzyloxycarbonyloxyethyl]-1β-methyl-1-carbadethiapen-2-em-3-carboxylic acid o-nitrobenzyl ester 7 (4 mg) in 4 ml H₂O and 4 ml dioxane is photolysized in a quartz tube under 3500 Å in the presence of NaHCO₃ (5 mg) at 20° C. for 2.5 hr. The mixture is extracted with ether. The aqueous layer is neutralized with HCl then concentrated to 1 ml. Chromatographic purification of the crude product by a XAD-2 resin (1.5×5 cm) eluting with water gives (I) (0.13 mg) as sodium salt. Electrophoresis shows single bioactive zone which moves 7.9 cm toward anode at 2 KV, for 20 min in 0.05 M pH 7.0 phosphate buffer.

STEP Mb

Following the procedure of Example 2, Steps G to M, except replacing the starting material as indicated, the isomeric products of 6-(1-hydroxyethyl)-1-methyl-1-carbadethiapen-2-em-3-carboxylic acid are obtained (TABLE V). (R is o-nitrobenzyloxycarbonyl.)

TABLE V

| Starting Material | Product |
|---|---|
| (structure with OR) | (structure with OH, CO₂H) |
| (structure with OR) | (structure with OH, CO₂H) |
| (structure with OR, alkyne) | (structure with OH, alkyne, CO₂H) |
| (structure with OR, alkyne) | (structure with OH, alkyne, CO₂H) |
| (structure with OR, alkyne) | (structure with OH, alkyne, CO₂H) |
| (structure with OR, alkyne) | (structure with OH, alkyne, CO₂H) |

EXAMPLE 3

Preparation of 8-oxo-2,2,5-trimethyl-7α-isopropyl-3-oxa-1-azabicyclo[4.2.0]octane

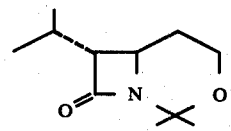

THF, 20 ml, is placed under N₂, treated with 1.54 ml diisopropylamine and cooled to −78° C. A solution of n-butyl lithium, 1.97 M in hexane (5.6 ml) is added dropwise over 5 min. The reaction mixture is stirred at −78° C. for 10 min and then treated with 8-oxo-2,2,5-trimethyl-3-oxa-1-azabicyclo[4.2.0]octane (1.55 g) in 15 ml THF which is added dropwise over 5 min. After another 10 min hexamethylphosphoramide (1.97 ml) is added. The mixture is stirred another 10 min, then treated with 2 ml of isopropyl iodide. The reaction mixture is stirred at −78° C. for 15 min and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C₆H₆ as eluant to give 8-oxo-2,2,5-trimethyl-7α-isopropyl-3-oxa-1-azabicyclo[4.2.0]octane.

EXAMPLE 4

Preparation of
8-oxo-2,2,5,7-tetramethyl-3-oxa-1-azabicyclo[4.2.0]octane

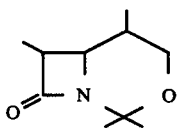

Following the procedure of Example 3, except substituting an equivalent amount of methyl iodide for the isopropyl iodide, the title compound is obtained.

EXAMPLE 5

Preparation of
8-oxo-2,2,5,7-tetramethyl-7-(hydroxymethyl)-3-oxa-1-azabicyclo[4.2.0]octane

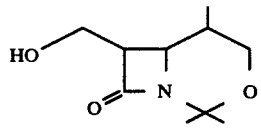

To a solution of 1.1 equivalents of freshly prepared lithium diisopropylamide in anhydrous tetrahydrofuran under a nitrogen atmosphere at −78° is added a solution of 8-oxo-2,2,5,7-tetramethyl-3-oxa-1-azabicyclo[4.2.0]octane in anhydrous tetrahydrofuran which has been cooled to −78° C. After two minutes, the resulting lithium enolate is treated with excess formaldehyde, introduced as a gas just above the surface of the stirred solution. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 8-oxo-2,2,5,7-tetramethyl-7-(hydroxymethyl)-3-oxa-1-azabicyclo[4.2.0]octane.

EXAMPLE 6

Preparation of
8-Oxo-2,2,5,7-tetramethyl-7-(o-nitrobenzylcarbonyldioxymethyl)-3-oxa-1-azabicyclo[4.2.0]octane

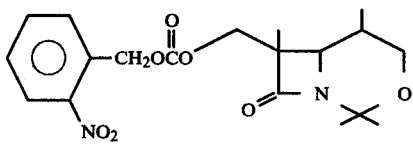

Under anhydrous conditions at 0° C. a solution of 8-oxo-2,2,5,7-tetramethyl-7-(hydroxymethyl)-3-oxa-1-azabicyclo[4.2.0]octane (60 mg) in 0.6 ml ether is treated with powdered potassium hydroxide (19 mg). After a period of 15 minutes, o-nitrobenzyl chloroformate (65 mg) is added to the reaction mixture. Stirring is continued at 25° C. for an additional 15 hours. The mixture is partitioned between 1 M pH 7 phosphate buffer and more ether. The ether phase is washed with water and brine, dried over magnesium sulfate and filtered. Evaporation of the filtrate under reduced pressure gives a colorless oil. Purification by preparation thick-layer chromatography on silica gel developing with 1:9 ethylacetate/benzene gives 8-oxo-2,2,5,7-tetramethyl-7-(o-nitrobenzylcarbonyldioxymethyl)-3-oxa-1-azabicyclo-[4.2.0]octane as a mixture of diastereomers.

EXAMPLE 7

Preparation of
3-methyl-3-(o-nitrobenzylcarbonyldioxymethyl)-4-(1-methyl-2-hydroxyethyl)-2-azetidinone

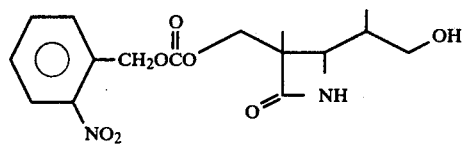

8-Oxo-3-oxa-2,2,5,7-tetramethyl-7-(1-o-nitrobenzylcarbonyldioxymethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give 3-methyl-3-(o-nitrobenzylcarbonyldioxymethyl)-4-(1-methyl-2-hydroxyethyl)-2-azetidinone as a mixture of diastereoisomers.

EXAMPLE 8

Examples 9–12 complement Examples 4, 5, 6 and 7 for the preparation of
3-methyl-3-(o-nitrobenzylcarbonyldioxymethyl)-4-(1-methyl-2-hydroxyethyl)-2-azetidinone

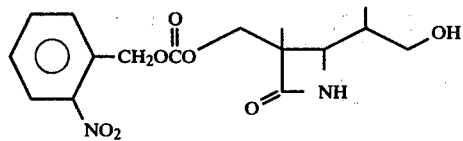

EXAMPLE 9

Preparation of
1-(2-Tetrahydropyranyl)-3-methyl-4-[1-methyl-2-(2-tetrahydropyranyl)oxyethyl]-2-azetidinone

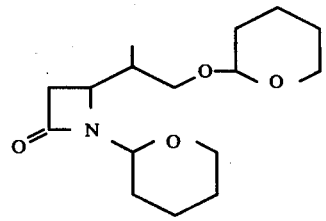

Under nitrogen and at 25° C., a solution of 3-methyl-4-(1-methyl-2-hydroxyethyl)-2-azetidinone (62 mg) in 0.5 ml of anhydrous p-dioxane is treated with 2,3-dihydropyran (0.98 ml) and p-toluensulfonic acid monohydrate (19 mg). The resulting solution is stirred for a period of 60 minutes and then partitioned between 10 ml of 0.5 M pH 7 phosphate buffer and 10 ml of ethyl acetate. The aqueous phase is extracted a second time with ethyl acetate. The combined ethyl acetate solutions are washed with brine, dried over magnesium sulfate and filtered. The filtrate is evaporated under reduced pressure to give the crude product. Purification by preparative thick-layer chromatography, developing with ethyl acetate, gives 1-(2-tetrahydropyranyl)-3-methyl-4-[1-methyl-2-(2-tetrahydropyranyl)-oxyethyl]-2-azetidinone.

Following the procedure of Example 9, the corresponding 3-methyl-1-(2-tetrahydropyranyl)-4-[1-methyl-2-(2-tetrahydropyranyl)oxyethyl]-2-azetidinone is obtained from the product of Example 4 via Example 7.

EXAMPLE 10

Preparation of 1-(2-tetrahydropyranyl)-3-methyl-3-(1-hydroxymethyl)-4-[1-methyl-2-(2-tetrahydropyranyl)-oxymethyl]-2-azetidinone

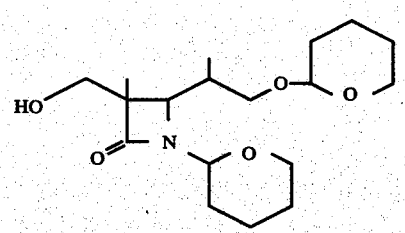

Following the procedure described for the preparation of 8-oxo-2,2,5,7-tetramethyl-7-(hydroxymethyl)-3-oxa-1-azabicyclo[4.2.0]octane from 8-oxo-2,2,5,7-tetramethyl-3-oxa-1-azabicyclo[4.2.0]octane (Example 5, above) and using 3-methyl-1-(2-tetrahydropyranyl)-4-[1-methyl-2-(2-tetrahydropyranyl)oxyethyl]-2-azetidinone one obtains a diastereomeric mixture of 1-(2-tetrahydropyranyl)-3-methyl-3-(hydroxymethyl)-4-[1-methyl-2-(2-tetrahydropyranyl)oxyethyl]-2-azetidinone.

EXAMPLE 11

Preparation of 3-Methyl-1-(2-tetrahydropyranyl)-3-(1-o-nitrobenzylcarbonyldioxymethyl)-4-[1-methyl-2-(2-tetrahydropyranyl)oxyethyl]-2-azetidinone

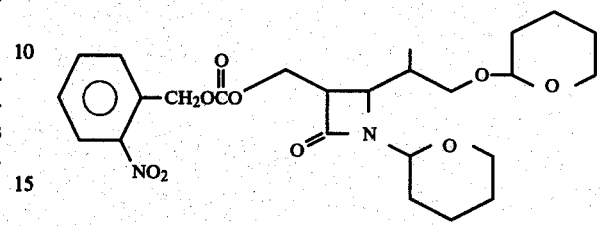

Following the procedure described for the preparation of 8-oxo-2,2,5,7-tetramethyl-7-(1-o-nitrobenzylcarbonyldioxymethyl)-3-oxa-1-azabicyclo[4.2.0]octane from 8-oxo-2,2,5,7-tetramethyl-7-(1-hydroxymethyl)-3-oxa-1-azabicyclo[4.2.0]octane and using 3-methyl-1-(2-tetrahydropyranyl)-3-(hydroxymethyl)-4-[1-methyl-2-(2-tetrahydropyranyl)oxyethyl]-2-azetidinone there is obtained 3-methyl-1-(2-tetrahydropyranyl)-3-(o-nitrobenzylcarbonyldioxymethyl)-4-[1-methyl-2-(2-tetrahydropyranyl)oxyethyl]-2-azetidinone.

EXAMPLE 12

Preparation of 3-Methyl-3-(o-nitrobenzylcarbonyldioxymethyl)-4-(1-methyl-2-hydroxyethyl)-2-azetidinone

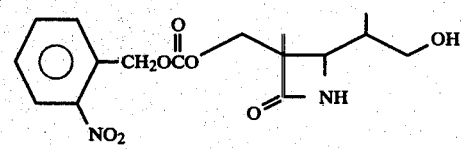

A solution of 3-methyl-1-(2-tetrahydropyranyl)-3-(o-nitrobenzylcarbonyldioxymethyl)-4-[1-methyl-2-(2-tetrahydropyranyl)-oxyethyl]-2-azetidinone in methanol at 25° C. is treated with 0.1 molar equivalents of p-toluenesulfonic acid monohydrate. The solution is stirred for a period of 2 hours and then neutralized with 1 M pH 7 phosphate buffer. The product is extracted into ethyl acetate. The ethyl acetate solution is washed with brine, dried over magnesium sulfate and filtered. The filtrate is evaporated under reduced pressure to give 3-methyl-3-(o-nitrobenzylcarbonyldioxymethyl)-4-(1-methyl-2-hydroxyethyl)-2-azetidinone.

EXAMPLE 13

Following the procedure of the foregoing Examples, the following substituted azetidinones useful in the preparation of the compound of the present invention are obtained.

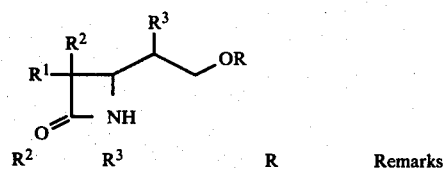

| $R^1$ | $R^2$ | $R^3$ | R | Remarks |
|---|---|---|---|---|

-continued $$R^1 \underset{O}{\overset{R^2}{-}} \underset{NH}{\overset{R^3}{-}} OR$$

| | $R^1$ | $R^2$ | $R^3$ | OR | Remarks |
|---|---|---|---|---|---|
| (1.) | 2-NO$_2$-C$_6$H$_4$-CH$_2$OC(=O)-OCH$_2$- | H | CH$_3$ | -Si- | Example 2, Step Fa-H, substitute acetaldehyde with formaldehyde in Step Fa. |
| (2.) | CH$_3$ | H | CH$_3$ | -Si- | Example 2, Steps Fa, G and H substitute acetaldehyde with methyl iodide. |
| (3.) | C$_6$H$_5$C(=O)- | H | CH$_3$ | -Si- | Example 2, Steps Fa and G-H, substitute acetaldehyde with benzoxyl chloride |
| (4.) | CH$_3$C(=O)- | H | CH$_3$ | -Si- | Example 2, Step Fa and G-H substitute acetaldehyde with acetyl chloride |
| (5.) | (CH$_3$)$_2$C(OH)- | H | CH$_3$ | -Si- | From (4), Ex. 2, Step Fa followed by reaction with MeMgBr |
| (6.) | (CH$_3$)CH(N$_3$)- | H | CH$_3$ | -Si- | Example 2, Step Fa followed by mesylation and displacement with N$_3$ |
| (7.) | CH$_3$CH(OCO$_2$CH$_2$-[2-NO$_2$-C$_6$H$_4$])- | CH$_3$ | CH$_3$ | -Si- | Product of Example 4 taken in Example 2, Fa-H. |
| (8.) | CH$_3$CH(OCO$_2$CH$_2$-[3-NO$_2$-C$_6$H$_4$])- | CH$_3$CH$_2$ | CH$_3$ | -Si- | Example 2, Step B, substitute 1' by its 2-ethyl analoque, followed by procedure of Example 13, No. 1 |

| | $R^1$ | $R^2$ | $R^3$ | $R^4$ | Remarks |
|---|---|---|---|---|---|
| (9.) | CH$_3$C(=O)- | CH$_3$ | CH$_3$ | -Si- | |
| (10.) | CH$_3$CH(OCO$_2$CH$_2$-[2-NO$_2$-C$_6$H$_4$])- | H | Et | -Si- | |
| (11.) | CH$_3$CH(OCO$_2$CH$_2$-[2-NO$_2$-C$_6$H$_4$])- | CH$_3$ | Et | -Si- | |
| (12.) | CH$_3$CH(OCO$_2$CH$_2$-[2-NO$_2$-C$_6$H$_4$])- | CH$_3$ | cyclopropyl | SiMe$_3$ | Use trimethylchlorosilane. |

-continued
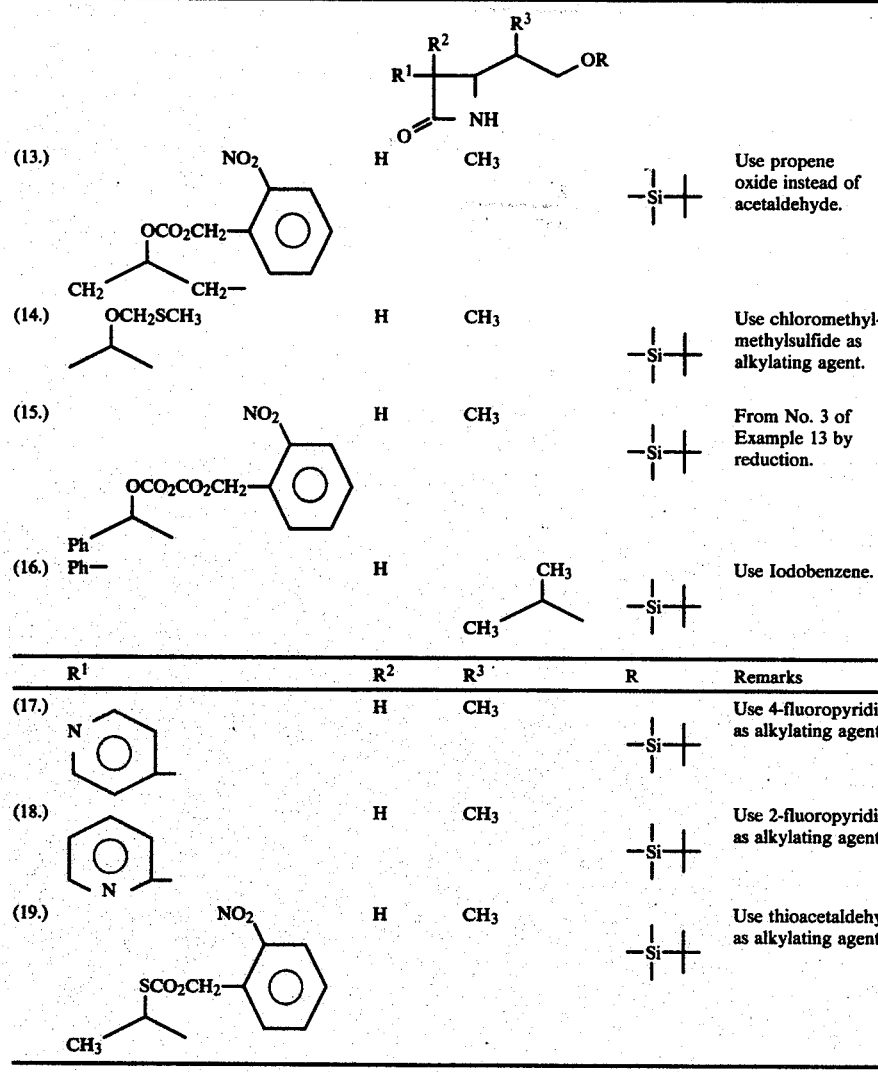
EXAMPLE 14
Following the foregoing text and Examples, the following species (I) are obtained by analogy.
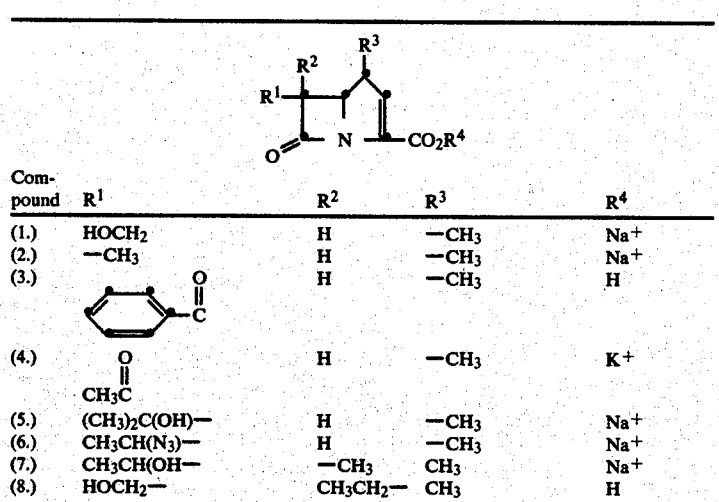
| Compound | $R^1$ | $R^2$ | $R^3$ | $R^4$ |
|---|---|---|---|---|
| (1.) | $HOCH_2$ | H | $-CH_3$ | $Na^+$ |
| (2.) | $-CH_3$ | H | $-CH_3$ | $Na^+$ |
| (3.) | (benzoyl group) | H | $-CH_3$ | H |
| (4.) | $CH_3C(O)-$ | H | $-CH_3$ | $K^+$ |
| (5.) | $(CH_3)_2C(OH)-$ | H | $-CH_3$ | $Na^+$ |
| (6.) | $CH_3CH(N_3)-$ | H | $-CH_3$ | $Na^+$ |
| (7.) | $CH_3CH(OH)-$ | $-CH_3$ | $CH_3$ | $Na^+$ |
| (8.) | $HOCH_2-$ | $CH_3CH_2-$ | $CH_3$ | H |

-continued

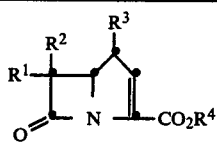

| Com-pound | R¹ | R² | R³ | R⁴ |
|---|---|---|---|---|
| (9.) | CH₃C(O)— | CH₃ | CH₃ | Na⁺ |
| (10.) | CH₃CH(OH)— | H | CH₃CH₂ | Na⁺ |
| (11.) | CH₃CH(OH)— | CH₃ | CH₃CH₂ | H |
| (12.) | HOCH₂— | CH₃ | cyclopropyl | Na⁺ |
| (13.) | CH₃CH(OH)CH₂— | H | CH₃ | (C₂H₅)₄N⁺ |
| (14.) | CH₃CH(OCH₂SCH₃)— | H | CH₃ | Na⁺ |
| (15.) | C₆H₅—CH(OH)— | H | CH₃ | Na⁺ |
| (16.) | C₆H₅— | H | CH₃CH(CH₃)— | Na⁺ |
| (17.) | 3-pyridyl | H | CH₃ | Na⁺ |
| (18.) | 3-pyridyl | H | CH₃ | Na⁺ |
| (19.) | CH₃CH(SH)— | H | CH₃ | K⁺ |

EXAMPLE 15

Preparation of Pharmaceutical Compositions

One such unit dosage form is prepared by mixing 120 mg. of 6-(1-hydroxyethyl)-1-methyl-1-carbadethiapen-2-em-3-carboxylic acid with 20 mg of lactose and 5 mg. of magnesium stearate. The 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 6-(1-hydroxyethyl)-1-methyl-1-carbadethiapen-2-em-3-carboxylic acid | 125 mg. |
| Cornstarch, U.S.P. | 6 mg. |
| Dicalcium Phosphate | 192 mg. |
| Lactose, U.S.P. | 190 mg. |
| Magnesium Stearate | balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 6-(1-hydroxyethyl)-1-methyl-1-carbadethiapen-2-em-3-carboxylic acid | 500 mg. |
| Sterile Water | 2 ml. |

| OPTHALMIC SOLUTION | | |
|---|---|---|
| 6-(1-hydroxyethyl-1-methyl-1-carbadethiapen-2-em-3-carboxylic acid | | 100 mg. |
| Hydroxypropylmethyl cellulose | | 5 mg. |
| Sterile Water | to | 1 ml. |

| OTIC SOLUTION | | |
|---|---|---|
| 6-(1-hydroxyethyl)-1-methyl-1-carbadethiapen-2-em-3-carboxylic acid | | 100 mg. |
| Benzalkonium chloride | | 0.1 mg. |
| Sterile Water | to | 1 ml. |

| TOPICAL OINTMENT | |
|---|---|
| 6-(1-hydroxyethyl)-1-methyl-1-carbadethiapen-2-em-3-carboxylic acid | 100 mg. |
| Polyethylene Glycol 4000 U.S.P. | 400 mg. |

| -continued | |
|---|---|
| TOPICAL OINTMENT | |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin, and kanamycin, or with other therapeutic agents such as probenecid.

What is claimed is:

1. A compound having the structure:

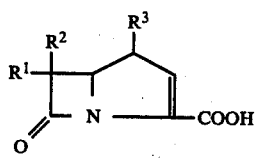

and the pharmaceutically acceptable salts thereof; wherein $R^1$, $R^2$ and $R^3$ are independently selected from the group consisting of hydrogen, and substituted and unsubstituted: alkyl having 1–6 carbon atoms, phenyl, phenylalkyl wherein the alkyl moiety has 1–6 carbon atoms, cycloalkyl and cycloalkylalkyl having 3 to 6 ring carbon atoms and 1–6 carbon atoms in the alkyl moiety; wherein the substituent or substituents on $R^1$, $R^2$ and $R^3$ are selected from chloro, bromo, fluoro, hydroxyl, amino, mono-, di-, and trialkylamino (each alkyl having 1–6 carbon atoms), alkoxyl having 1–6 carbon atoms, cyano and carboxyl; wherein $R^3$ is not hydrogen and $R^1$ and $R^2$ are not both hydrogen at the same time.

2. A compound according to claim 1 wherein $R^3$ is alkyl, cyclopropyl, benzyl or phenyl; $R^1$ is hydrogen and $R^2$ is alkyl or phenylalkyl substituted by hydroxyl or amino.

3. A compound according to claim 2 wherein $R^3$ is methyl, ethyl, isopropyl, t-butyl or phenyl and $R^2$ is 1-hydroxyethyl, methyl, or hydroxymethyl.

4. An antibiotic pharmaceutical composition comprising a therapeutically effective amount of a compound according to claim 1 and a pharmaceutical carrier therefor.

* * * * *